US 11,617,620 B2

(12) United States Patent
Tran et al.

(10) Patent No.: US 11,617,620 B2
(45) Date of Patent: Apr. 4, 2023

(54) SYSTEMS AND METHODS FOR IDENTIFYING ANATOMICALLY RELEVANT BLOOD FLOW CHARACTERISTICS IN A PATIENT

(71) Applicant: HeartFlow, Inc., Redwood City, CA (US)

(72) Inventors: Amy Tran, Redwood City, CA (US); Greg Hart, Redwood City, CA (US); Heather Brown, Redwood City, CA (US); Michiel Schaap, Redwood City, CA (US); Rhea Tombropoulos, Woodside, CA (US); Sethuraman Sankaran, Palo Alto, CA (US)

(73) Assignee: HeartFlow, Inc., Redwood City, CA (US)

( * ) Notice: Subject to any disclaimer, the term of this patent is extended or adjusted under 35 U.S.C. 154(b) by 433 days.

(21) Appl. No.: 15/904,008

(22) Filed: Feb. 23, 2018

(65) Prior Publication Data
US 2018/0243033 A1    Aug. 30, 2018

Related U.S. Application Data

(60) Provisional application No. 62/463,336, filed on Feb. 24, 2017.

(51) Int. Cl.
*A61B 34/10* (2016.01)
*A61B 8/04* (2006.01)
(Continued)

(52) U.S. Cl.
CPC .............. *A61B 34/10* (2016.02); *A61B 5/026* (2013.01); *A61B 5/02007* (2013.01);
(Continued)

(58) Field of Classification Search
CPC ...... A61B 34/10; A61B 5/02007; A61B 5/026; A61B 5/7264; A61B 5/743; A61B 5/7435;
(Continued)

(56) References Cited

U.S. PATENT DOCUMENTS 8,315,812 B2    11/2012    Taylor
8,958,623 B1 *   2/2015    Grady ..................... G09B 9/00
                                                    382/131

(Continued)

FOREIGN PATENT DOCUMENTS

EP          2 484 285 A1      8/2012
EP          2 963 574 A2      1/2016
WO    WO 2014/064702 A2       5/2014

OTHER PUBLICATIONS

Sankaran Sethuraman et al. "HALE: Healthy Area of Lumen Estimation for Vessel Stenosis Quantification", Oct. 2, 2016, pp. 380-387.

*Primary Examiner* — Patrick Fernandes
*Assistant Examiner* — Joseph A Tombers
(74) *Attorney, Agent, or Firm* — Bookoff McAndrews, PLLC

(57) ABSTRACT

Systems and methods are disclosed for identifying anatomically relevant blood flow characteristics in a patient. One method includes: receiving, in an electronic storage medium, a patient-specific representation of at least a portion of vasculature of the patient having a lesion at one or more points; receiving values for one or more metrics of interest associated with one or more locations in the vasculature of the patient; receiving one or more observed lumen measurements of the vasculature of the patient; determining the location of a diseased region in the vasculature of the patient using the received values for the one or more metrics of interest, wherein the determination of the location (Continued)

includes predicting or receiving one or more healthy lumen measurements of the vasculature of the patient; determining the extent of the diseased region; and generating a visualization of at least the diseased region.

20 Claims, 11 Drawing Sheets

(51) Int. Cl.
*A61B 8/06* (2006.01)
*A61B 6/00* (2006.01)
*A61B 8/08* (2006.01)
*G06T 7/00* (2017.01)
*G16H 30/20* (2018.01)
*A61B 5/026* (2006.01)
*A61B 5/00* (2006.01)
*A61B 5/02* (2006.01)
*A61B 90/00* (2016.01)
*A61B 5/021* (2006.01)

(52) U.S. Cl.
CPC ............ *A61B 5/7264* (2013.01); *A61B 5/743* (2013.01); *A61B 5/7435* (2013.01); *A61B 6/507* (2013.01); *A61B 6/5217* (2013.01); *A61B 8/04* (2013.01); *A61B 8/06* (2013.01); *A61B 8/5223* (2013.01); *G06T 7/0012* (2013.01); *G16H 30/20* (2018.01); *A61B 5/021* (2013.01); *A61B 2034/105* (2016.02); *A61B 2090/374* (2016.02); *A61B 2090/3735* (2016.02); *A61B 2090/3762* (2016.02); *A61B 2090/3784* (2016.02); *A61B 2505/05* (2013.01); *A61B 2576/023* (2013.01); *G06T 2207/10084* (2013.01); *G06T 2207/30104* (2013.01)

(58) Field of Classification Search
CPC ......... A61B 6/507; A61B 6/5217; A61B 8/04; A61B 8/06; A61B 8/5223; A61B 2034/105; A61B 2090/3735; A61B 2090/374; A61B 2090/3762; A61B 2090/3784; A61B 5/021; A61B 2505/05; A61B 2576/023; G16H 30/20; G06T 7/0012; G06T 2207/10084; G06T 2207/30104
See application file for complete search history.

(56) References Cited

U.S. PATENT DOCUMENTS

| | | | |
|---|---|---|---|
| 2014/0236011 A1 | 8/2014 | Fan et al. | |
| 2015/0066818 A1* | 3/2015 | Choi | G06N 7/005 706/12 |
| 2015/0324962 A1* | 11/2015 | Itu | G06T 7/00 382/130 |
| 2016/0042144 A1* | 2/2016 | Sankaran | A61B 6/5217 703/11 |
| 2016/0157802 A1* | 6/2016 | Anderson | A61B 6/4417 600/407 |

* cited by examiner

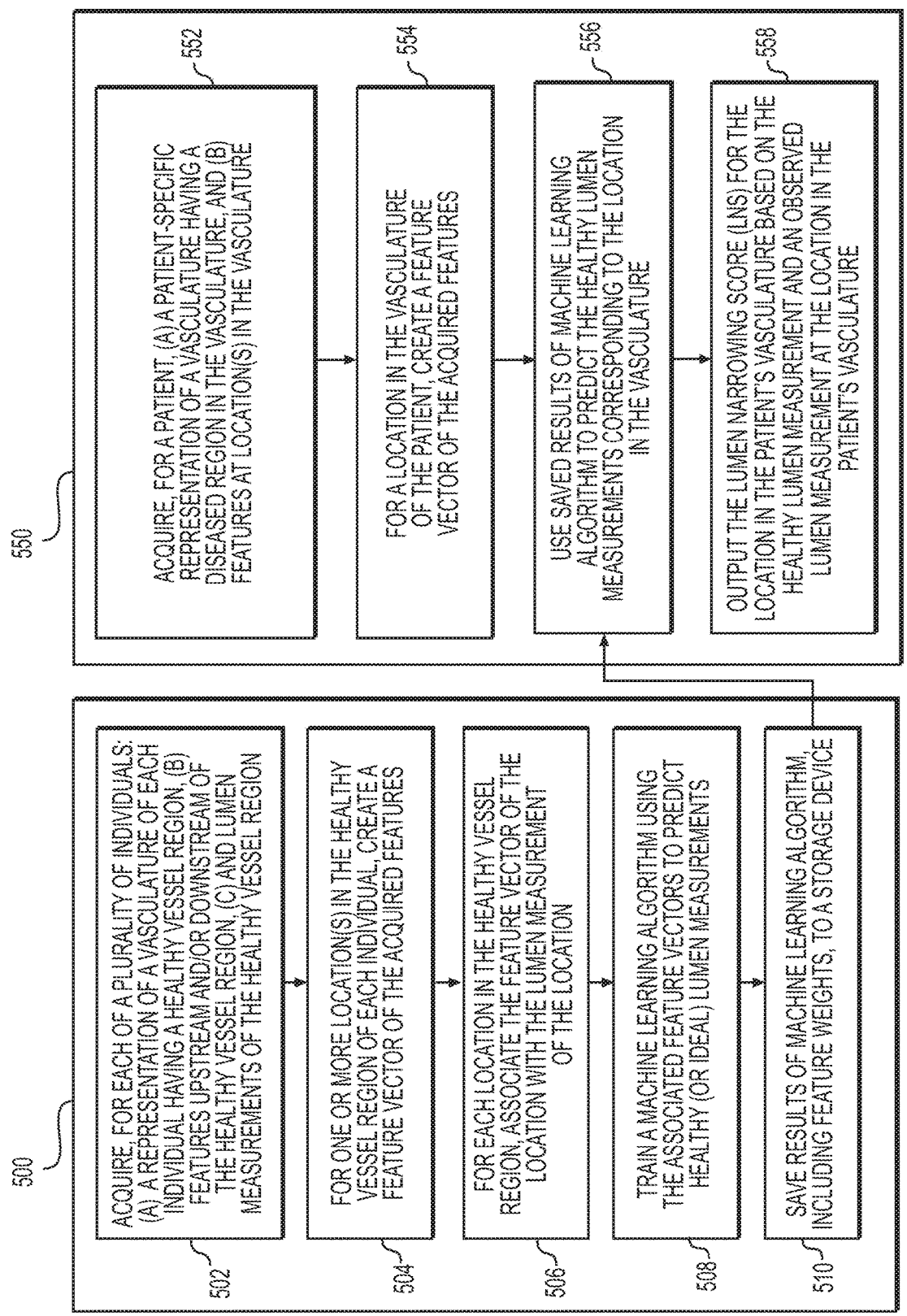

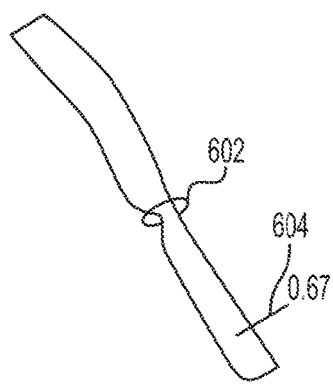
FIG. 6A
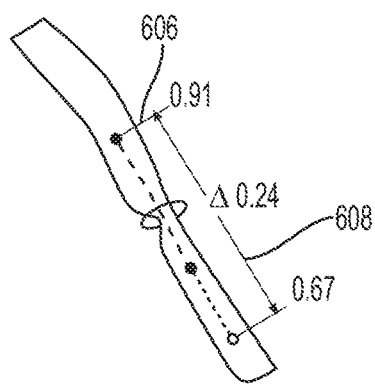
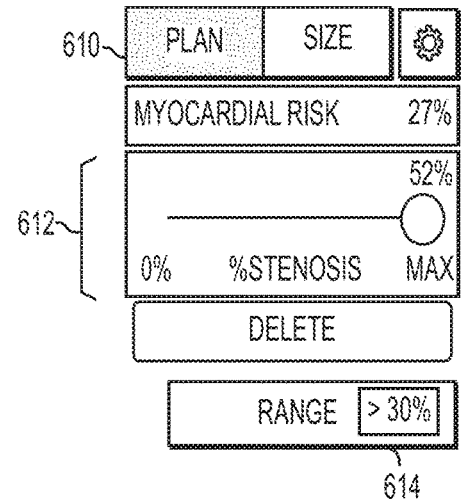
FIG. 6B
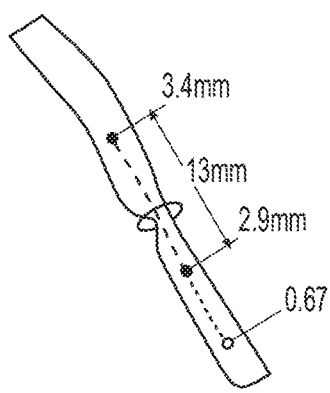
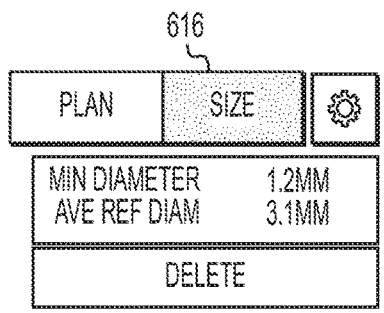
FIG. 6C

SYSTEMS AND METHODS FOR IDENTIFYING ANATOMICALLY RELEVANT BLOOD FLOW CHARACTERISTICS IN A PATIENT

RELATED APPLICATION(S)

This application claims priority to U.S. Provisional Application No. 62/463,336 filed Feb. 24, 2017, the entire disclosure of which is hereby incorporated herein by reference in its entirety.

FIELD OF THE DISCLOSURE

Various embodiments of the present disclosure relate generally to diagnostics and treatment planning of vascular system(s). More specifically, particular embodiments of the present disclosure relate to systems and methods for identifying anatomically relevant blood flow characteristics in a patient.

BACKGROUND

Various metrics may be used by medical personnel (e.g., nurse, physician, surgeon, medical specialist, etc.) to diagnose, assess the severity of, and/or plan treatments for a lesion. Although values associated with these metrics may be measured and/or calculated throughout the patient's vasculature, the medical personnel may face challenges in identifying the relevant values in order to diagnose, assess, and/or plan treatments for the patient. For example, there may be limitations to merely using lumen size to identify diseased vessel regions, because regions of a vasculature that have lumen narrowing may not be functionally significant. Similarly, there may be limitations to using any blood flow characteristics to plan for vascular treatments, as aberrant blood flow characteristics may not necessarily entail the presence of disease. There is thus a desire to differentiate anatomically relevant blood flow characteristics and similar measurements from irrelevant characteristics. Identifying relevant values would greatly improve patient care, as physicians may consider whether to make local treatments by invasive means (e.g., a stent, bypass, etc.) or broader treatments that are non-invasive (e.g., optimum medical therapy). Therefore, there is a need to provide a better understanding of the impact of vascular disease on a vessel, in the context of an entire patient profile. In particular, there is also a desire to isolate blood flow characteristics pertinent to treatment for each patient.

In addition, simulation-based estimations of metrics of interest may demand a substantial computational burden that can make these virtual, noninvasive tests difficult to execute in a real-time clinical environment. Consequently, there is also a desire for new approaches for performing rapid, noninvasive estimations of various metrics of interest and/or anatomical information that are computationally inexpensive.

SUMMARY

Described below are various embodiments of the present disclosure of systems and methods for identifying anatomically relevant blood flow characteristics in a patient.

One method includes: receiving, in an electronic storage medium, a patient-specific representation of at least a portion of vasculature of the patient having a lesion at one or more points; receiving values for one or more metrics of interest associated with one or more locations in the vasculature of the patient; determining a diseased region in the vasculature of the patient using the received values for the one or more metrics of interest; determining a length or severity of the diseased region; generating a visualization of at least the diseased region; and outputting one or more selected values of the one or more metrics of interest, where the one or more selected values are associated with the diseased region.

In accordance with another embodiment, a system for identifying anatomically relevant blood flow characteristics in a patient comprises: a data storage device storing instructions for identifying anatomically relevant blood flow characteristics in a patient; and a processor configured for: receiving, in an electronic storage medium, a patient-specific representation of at least a portion of vasculature of the patient having a lesion at one or more points; receiving values for one or more metrics of interest associated with one or more locations in the vasculature of the patient; determining a diseased region in the vasculature of the patient using the received values for the one or more metrics of interest; determining a length or severity of the diseased region; generating a visualization of at least the diseased region; and outputting one or more selected values of the one or more metrics of interest, where the one or more selected values are associated with the diseased region.

In accordance with another embodiment, a non-transitory computer readable medium for use on a computer system containing computer-executable programming instructions for identifying anatomically relevant blood flow characteristics in a patient, the method comprising: receiving, in an electronic storage medium, a patient-specific representation of at least a portion of vasculature of the patient having a lesion at one or more points; receiving values for one or more metrics of interest associated with one or more locations in the vasculature of the patient; determining a diseased region in the vasculature of the patient using the received values for the one or more metrics of interest; determining a length or severity of the diseased region; generating a visualization of at least the diseased region; and outputting one or more selected values of the one or more metrics of interest, where the one or more selected values are associated with the diseased region.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments, and together with the description, serve to explain the principles of the disclosed embodiments.

FIG. 4B may be referenced in various steps of method 400, as depicted in FIG. 4A. and/or in various steps of method 500, as depicted in FIG. 5

FIG. 5 is a block diagram of a general method 500 of predicting a healthy (or ideal) lumen radius using a machine learning algorithm.

FIGS. 6A-6H are illustrations of exemplary user interfaces for identifying an analyzing anatomically relevant blood flow characteristics in a patient.

Figure 1:
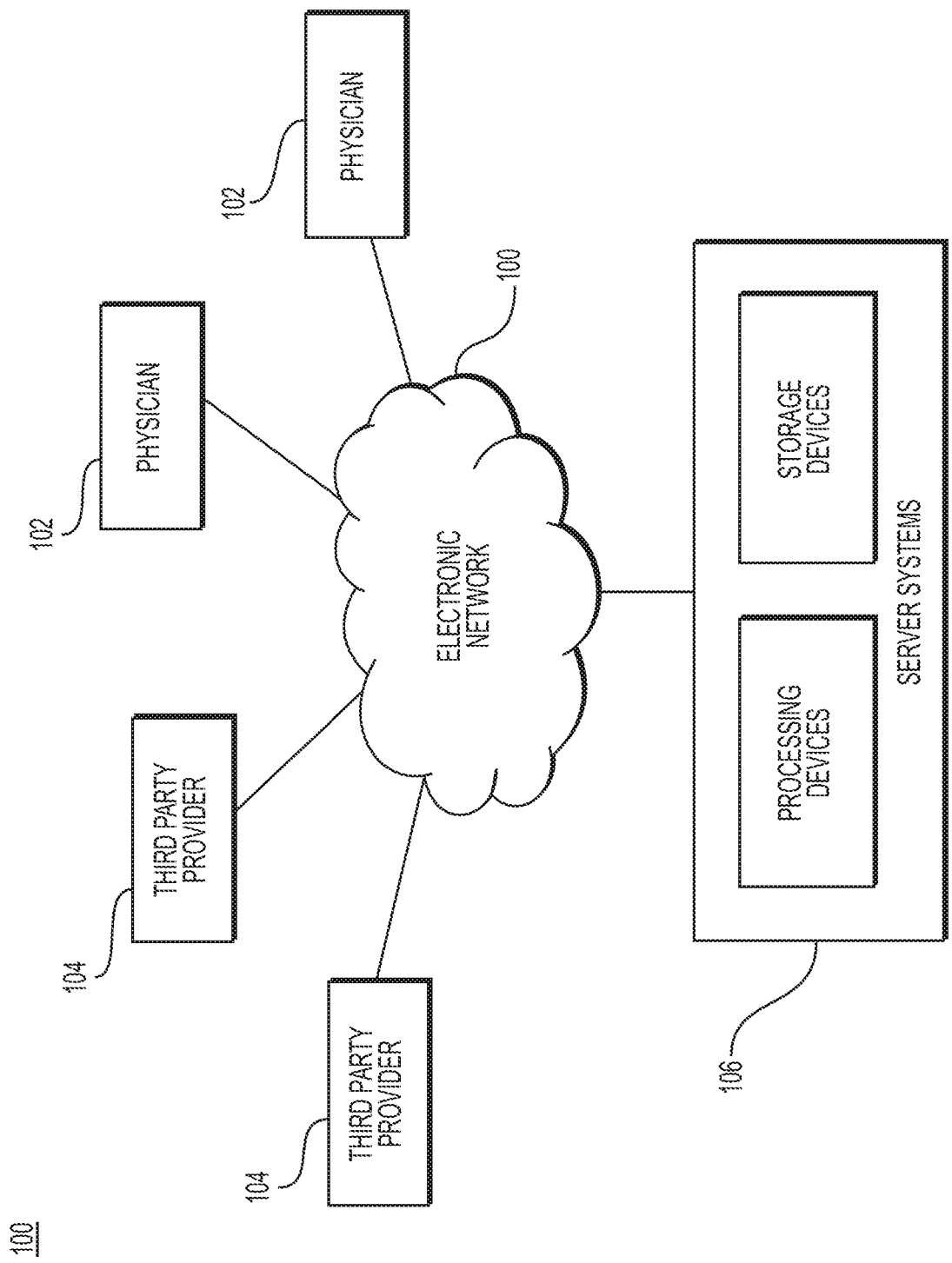
FIG. 1 is a block diagram of an exemplary system and network 100 for identifying anatomically relevant blood flow characteristics in a patient, according to an exemplary embodiment of the present disclosure.

The steps described in the methods may be performed in any order, or in conjunction with any other step. It is also contemplated that one or more of the steps may be omitted for performing the methods described in the present disclosure.

DESCRIPTION OF THE EMBODIMENTS

Reference will now be made in detail to the exemplary embodiments of the disclosure, examples of which are illustrated in the accompanying drawings. Wherever possible, the same reference numbers will be used throughout the drawings to refer to the same or like parts.

Various embodiments of the present disclosure may provide systems and methods for identifying anatomically relevant blood flow characteristics in a patient. The anatomical relevance of these blood flow characteristics may be based on their proximity towards or location within diseased region(s). For purposes of this disclosure, blood flow characteristics may include, but are not limited to, blood pressure, fractional flow reserve (FFR), computational tomography derived fractional flow reserve (FFR-CT), blood flow rate or flow velocity, a velocity or pressure field, hemodynamic forces, and organ and/or tissue perfusion characteristics. In some embodiments, anatomically relevant blood flow characteristics may further include a function of FFR or FFR-CT, for example, an FFR (or FFR-CT) gradient, distal point of FFR (or FFR-CT) recovery, proximal point of FFR (or FFR-CT) recovery, delta of FFR (or FFR-CT), etc.

These anatomically relevant blood flow characteristics may be visualized on user interfaces (as depicted in FIGS. 6A-6H), and may enable a user to track the anatomically relevant blood flow characteristics using visual pins, providing an improvement to medical diagnostics, treatment planning, and patient care.

The blood flow characteristics may be rendered as anatomically relevant by being situated within the location(s), range, and/or extent of diseased region(s). The diseased region(s) may be located, and their extent or range may be determined using metrics of interest. These metrics may be used to track the location of diseased regions and assess the range or extent (e.g., vascular length or disease severity) of a diseased region by determining, for example, a stenosis location, and various anatomical or geometric characteristics (e.g., length, diameters, vessel or lumen narrowing, etc.).

For example, a lumen narrowing score (LNS) may help track the location of the diseased region(s), by comparing a lumen's actual measurements to a healthy or idealized measurement. Even further, some metrics of interest may provide improvements in medical diagnostics and/or treatment planning due to their ability to replicate the precision of other metrics of interest (e.g., FFR). The use of these metrics to track the locations of diseased region(s), and thereby present anatomically relevant blood flow characteristics, may be aided by kernel regression and machine learning based methods. Moreover, machine learning based methods of computation may overcome the computational burden and posed by simulation-based estimations, and help facilitate rapid, noninvasive estimations of various metrics of interest and/or anatomical information Anatomically relevant blood flow characteristics (e.g., FFR) may be used to assess a diseased region or tissue (e.g., via determining a percentage of stenosis, a percentage of myocardium at risk, etc.), or assess treatment options. At least some embodiments of the present disclosure may identify one or more highly relevant locations associated with disease in order to provide the medical personnel the most pertinent information of the metric values at, or based on, those identified locations. Furthermore, the systems and methods of the present disclosure may apply to patients with cardiovascular disease in various vessel systems in the body (e.g., coronary arteries, cerebral arteries, peripheral arteries, renal arteries, etc.).

Referring now to the figures, FIG. 1 depicts a block diagram of an exemplary system 100 and network for identifying anatomically relevant blood flow characteristics in a patient, according to an exemplary embodiment. Specifically, FIG. 1 depicts a plurality of physicians 102 and third party providers 104, any of whom may be connected to an electronic network 100, such as the Internet, through one or more computers, servers, and/or handheld mobile devices. Physicians 102 and/or third party providers 104 may create or otherwise obtain images of one or more patients' anatomy. The physicians 102 and/or third party providers 104 may also obtain any combination of patient-specific and/or reference anatomical images, physiological measurements, and/or information, including, but not limited to, geometrical and/or anatomical characteristics of the vessels of interest of a patient, blood flow characteristics, impedance values for vessels of interest, measurements of the vessel or lumen, plaque characteristics, etc. In some embodiments, physicians 102 and/or third party providers 104 may also obtain reference values pertaining to blood flow characteristics or metrics of interest. For example, physicians 102 and/or third party providers 104 may obtain population-based or reference data related to healthy lumen measurements or metrics of interest from a library of parameters or a look-up table based on the anatomical, physiological, geometric, or biographical features.

Physicians 102 and/or third party providers 104 may transmit the anatomical images, physiological information, and/or information on vessels of interest to server systems 106 over the electronic network 100. Server systems 106 may include storage devices for storing images and data received from physicians 102 and/or third party providers 104. Server systems 106 may also include processing devices for processing images and data stored in the storage devices.

Figure 2:
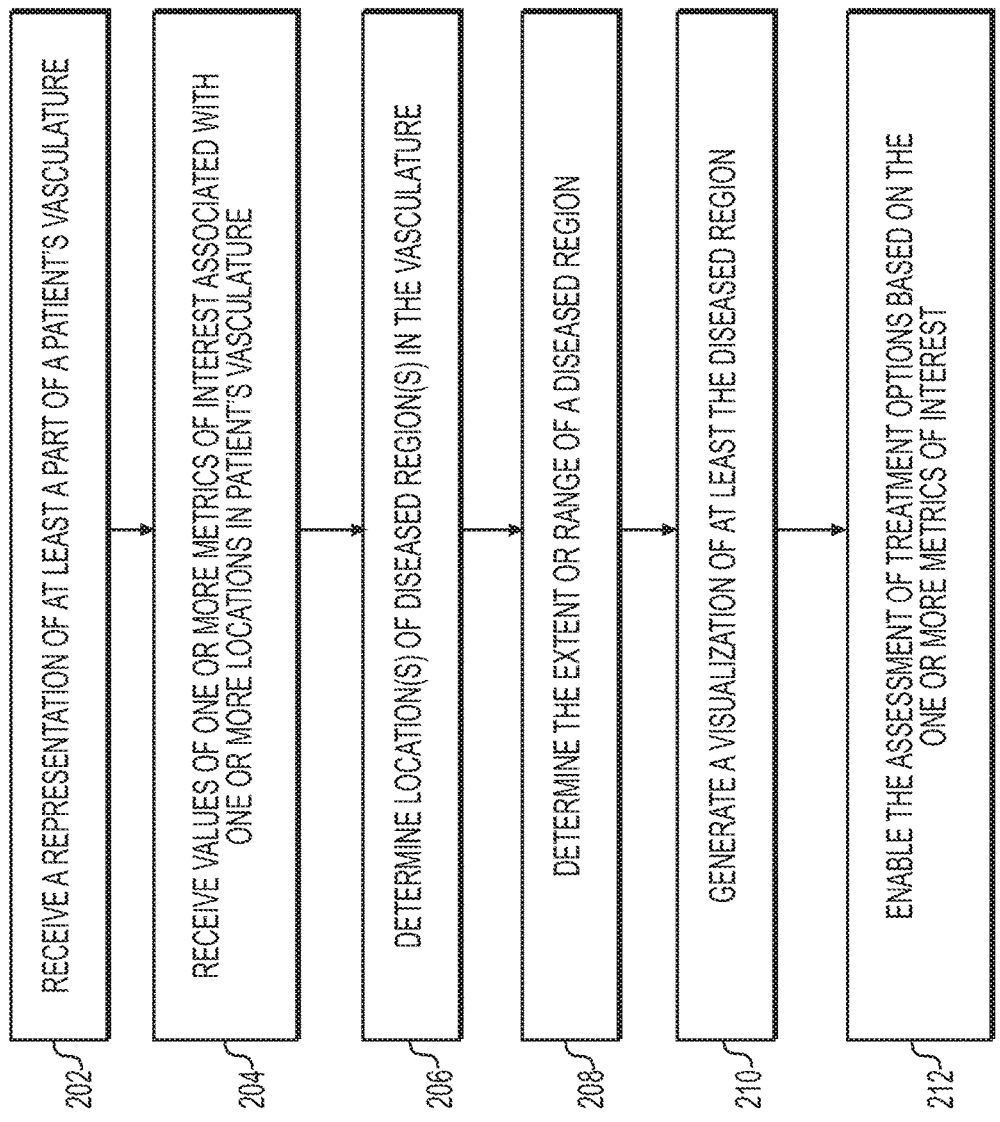
FIG. 2 is a block diagram of a general method 200 of identifying anatomically relevant blood flow characteristics in a patient, according to an exemplary embodiment of the present disclosure.

FIG. 2 depicts a method 200 of identifying anatomically relevant blood flow characteristics in a patient, according to an exemplary embodiment of the present disclosure. In some embodiments, step 202 of method 200 may include receiving a representation of at least a part of a patient's vasculature.

In some embodiments, step 202 may include receiving a representation comprising patient-specific image data of a vascular system, vasculature, or a vessel of interest of a patient. For example, the image data may be received from computerized tomography (CT), magnetic resonance imaging (MRI), ultrasound, intravenous ultrasound (IVUS), optical coherence tomography (OCT), etc.

The vascular system, vessel of interest, or vasculature may belong to a coronary, cerebral, peripheral, hepatic, renal, or visceral vasculature. The vascular model may include any vessels that may be prone to stenotic lesions or plaque formation. In some embodiments, other patient data of the vascular system, vasculature, or the vessel of interest of the patient may be received, for example, measured blood flow characteristics and/or properties. The image data and/or blood flow characteristics and/or properties may be non-invasively and/or invasively acquired from a patient (e.g., via a scanning modality or medical device), or may be acquired via population studies (e.g., based on similarities with the patient).

In some embodiments, the representation may include a patient-specific anatomic model of a vascular system, vasculature, or vessel of interest of a patient. The model may be a vascular model of one or more dimensions (e.g., one-dimensional, two-dimensional, three-dimensional, four-dimensional, etc.) parameterized by vessel centerline location coordinates. For example, the representation may include a reduced order or lumped parameter model where the vasculature is likened to an electric circuit according to methods disclosed, for example, in U.S. Pat. No. 8,315,812 issued Nov. 20, 2012, entitled "Method and System for Patient-Specific Modeling of Blood Flow," which is incorporated by reference in its entirety.

Step 204 may include receiving the values of one or more metrics of interest associated with one or more locations in the patient's vasculature. The metrics and/or their values may include, but are not limited to, one or more of: a calculated or measured fractional flow reserve (FFR) value; a calculated or measured instant wave free ratio (iFR); a calculated or measured coronary flow reserve (CFR) value; anatomical characteristics, including, for example, a vessel size (e.g., diameter, area, etc.), vessel thickness, vessel wall properties, vessel torsion, vessel bifurcations, etc.; a plaque characteristic (e.g., local calcium score, local low intensity plaque score, a measure of spotty calcification, remodeling index, a presence or absence of plaque signs such as the napkin ring sign, etc.); metrics for radiodensity, for example, a depiction, histogram, calculation, or measurement of in Hounsfield Units (HU); and/or a blood flow characteristic, e.g., a blood flow rate or velocity, a blood pressure, etc. In some embodiments, the metrics of interest may further include hemodynamic forces acting on the vessel walls or diseased regions (e.g., wall shear stress, axial plaque stress, etc.)

While the metrics of interest may include blood flow characteristics, the metrics of interest may not necessarily be anatomically relevant. For example, these metrics of interest may not be located at or within a desired proximity to a diseased region, and/or may not be predictive of the characteristics of the disease. Various embodiments of the present disclosure may provide methods for using the metrics of interest to determine the location(s), extent, and/or range of diseased region(s) (e.g., using kernel regression and/or machine learning), and thereby determine anatomically relevant blood flow characteristics. It is contemplated that in some embodiments, for example, where a general location of a diseased region is already evident from a representation of the vasculature, step 204 may be performed to confirm or gain more precise location(s) of the diseased region(s).

Step 206 may include determining location(s) of diseased region(s) in the vasculature. A diseased region may refer to, for example, a lesion, a stenosis, and/or a plaque in the vasculature. Method 400, as depicted in FIG. 4 may provide further details for at least some embodiments for performing step 206. A location may include one or more of a point, area, volume, cross-section, segment, or region within the vasculature. Furthermore a section or region of the vessel may be based on the splitting or segmentation of the vessel based on anatomical, geometrical or image-related features (e.g., intensity variations).

Figure 3:
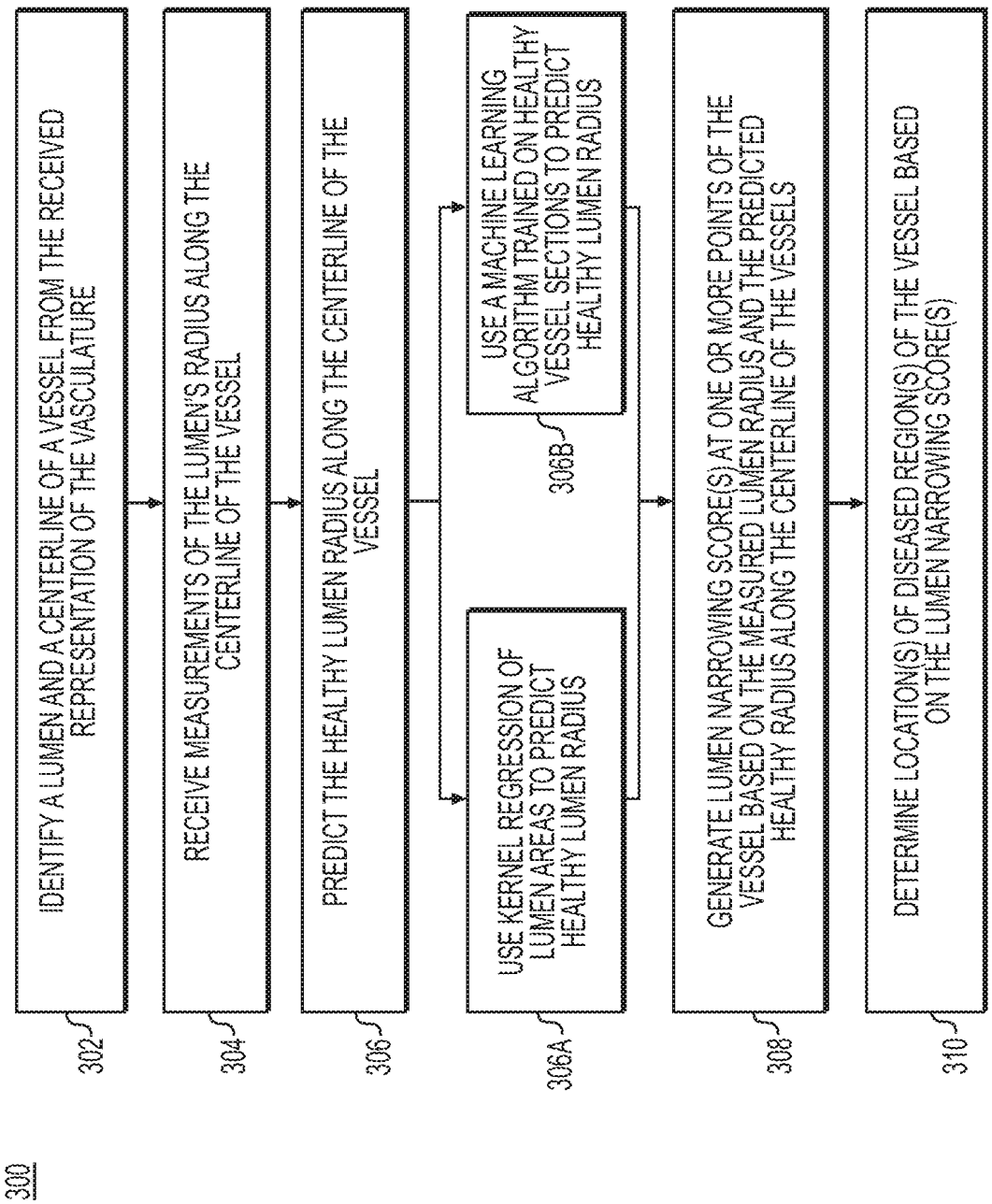
FIG. 3 is a block diagram of a general method 300 of determining location(s) of diseased region(s) in the vasculature, according to an exemplary embodiment of the present disclosure.
Figure 4A:
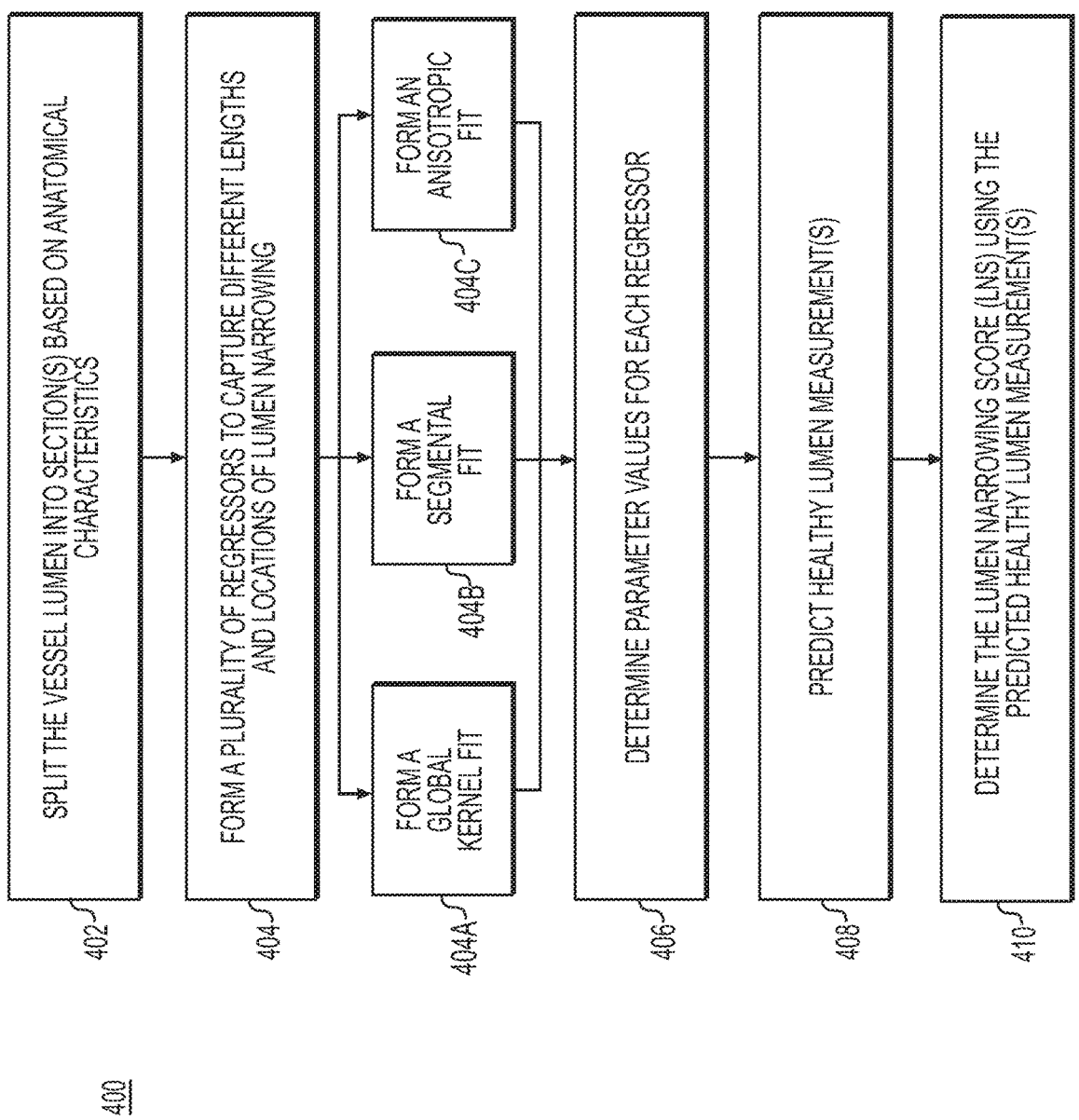
FIG. 4A is a block diagram of a general method 400 of predicting a healthy (or ideal) lumen radius using kernel regression.

In one embodiment, step 206 may include identifying location(s) of vessel narrowing or lumen narrowing, as diseased vessel location(s) or region(s). For example, step 206 may include a comparison of an observed or actual measurement of a lumen to a reference measurement of the lumen (e.g. a healthy lumen size) at one or more points of the vasculature. In some embodiments, the measurement may be of vessel diameter, radius, or size, or a measurement of the vessel wall. The actual lumen measurement and/or reference measurement may be calculated, measured, and/or obtained. In some embodiments, step 206 may involve a kernel regression technique to find lumen narrowing. The kernel regression techniques may be used on lumen area profiles from the ostium to the leaves of the vasculature. A kernel regression technique may be described further in step 306A of method 300, as depicted in FIG. 3, and may be further described in method 400, as depicted in FIG. 4A. In other embodiments, step 206 may involve a machine learning method. The machine learning method may use a database of healthy vessel sections and may map geometric features (e.g., average downstream area, crown volume, ratio of volume to length, etc.), as well as physiology-derived features (e.g., Murray's law describing the relationship between parent to daughter vessels in healthy vasculature). At least one machine learning based method for determining the location may be described in step 306B of method 300, as depicted in FIG. 3, and further described in method 500, as depicted in FIG. 5.

In yet another embodiment, step 206 may involve the use of a plaque characteristic metric. The plaque characteristic metric may include, for example, a calcified plaque score or a local plaque burden to determine the location(s) of the diseased regions. Thus, a plaque characteristic metric that may exceed a predetermined or reference threshold may indicate the presence or location of a diseased region.

Step 208 may include determining the extent or range of the diseased region. For example, step 208 may include determining one or more locations in the vessel proximal to and/or distal to the lesion in which the acuity of the lesion (e.g., a degree of vessel or lumen narrowing, a lumen narrowing score (LNS), etc.) is no longer present in the vessel. This step may be accomplished with various methods or combination of methods.

In one embodiment, the extent or range may be based on a fixed distance proximal or distal to the detected lesion. This distance may be predetermined or selected by a user on a user interface. For example, for any given lesion, the range of the diseased region comprising the lesion may be assigned to be x millimeters proximal or distal to the determined location of the diseased region (e.g., of step 206). In other embodiments, the fixed distance may be based on the severity of the lesion (e.g., a plaque characteristic). Thus a more severe lesion may be part of a disease region that would span a greater distance proximal and distal to the detected lesion.

If, for example, there is a lesion at a bifurcation of a vessel, step 208 may involve identifying two locations, e.g., a location on each of the daughter branches, and/or identifying a location upstream in the parent branch. The daughter branches may refer to the two vessels downstream of the bifurcation while the parent vessel may refer to the vessel upstream of the bifurcation leading to the daughter branches. Step 208 may include designating the region between the two locations as the diseased region.

In some embodiments, the extent or range may accommodate for serial lesions. Serial lesions may refer to situations where there are two or more lesions along a vessel path. In scenarios where the distance between two lesions for a serial lesion falls below a predetermined distance value, a location distal to the distal lesion may be appropriate for treatment planning. In such embodiments, step 208 may include determining a diseased region as spanning the length between a location distal to a distal lesion of a set of serial lesions, to a location proximal to a proximal lesion of the set of serial lesions.

Determining the extent or range of a diseased region may also include determining the stability and/or recovery of a computed, measured, and/or obtained blood flow characteristic, including but not limited to, FFR, iFR, CFR, etc. Sometimes, blood flow characteristics may change variably along the length of the vessel, for instance, in regions just distal to the "throat" of a stenosis, e.g., the point with the lowest diameter. In such regions, the metric of interest may have high sensitivity to a probed location. Recovery may refer to such regions of high sensitivity that may be distal to the throat of a stenosis. Thus, it is contemplated that metrics may be computed in regions which may be less sensitive to small changes in location (e.g.,) region of stable blood flow. Furthermore, step 208 may include determining the stability and/or recovery of a hemodynamic quantity of interest.); and/or using anatomical landmark(s)

Step 210 may include generating a visualization of at least the diseased region. In some embodiments, step 210 may include outputting to an electronic storage medium and/or displaying the value(s) of the metric(s) of interest at the location(s) determined in steps 206 or 208, which are proximal to and/or distal to the lesion(s). The output may have several forms, including, but not limited to, e.g., placing visual pin(s) displaying the value of the metric at the determined location(s) that are proximal to and/or distal to the diseased region(s), or that show the extent or range of the diseased region(s). An exemplary visualization may also include the determined values of the metric at the identified location(s), e.g. in a table, graph, histogram, etc. FIGS. 6A-6H may describe additional and/or alternate functionalities of user interface providing this visualization in further detail.

In some embodiments, step 210 may include outputting, to an electronic storage medium and/or display, a function of the metric(s) of interest. The function(s) of the metric(s) of interest may be between the location(s) that are proximal to the diseased region(s) and location(s) that are distal to the diseased region(s), or may show the extent or range of the diseased region(s). A function of the metric of interest may also include the change in the values of a metric between the location(s) that are proximal to the lesion(s) and location(s) that are distal to the lesion(s). For example, a blood pressure value may be higher proximal to a lesion and lower distal to the lesion. The outputted results or metrics of interest may include blood flow characteristics overlaid on a representation of a vasculature. Furthermore, the results may be visualized using color maps.

The visualization may include a scale or key may be provided that indicates which numerical values of the metrics of interest correspond to which colors, shades, patterns, or other visual indicators. For example, a representation of the vasculature may be provided in color, and a color spectrum may be used to indicate variations in computed metric of interest (e.g., FFR, LNS, etc.) throughout the representation of the vasculature. The color spectrum may include red, yellow, green, cyan, and blue, in order, e.g., from the highest LNS to lowest LNS. For example, the upper limit (red) may indicate an LNS of 100%, and the lower limit (red) may indicate a value of 30%, with green indicating approximately intermediate values. For example, the lower limit may be used for determining whether the computed LNS indicates a functionally significant lesion or other feature that may require intervention. Thus, the representation for some patients may show a majority or all of the aorta as blue or other color towards the higher end of the spectrum, and the colors may change gradually through the spectrum (e.g., towards the lower end of the spectrum (down to anywhere from red to blue) towards the distal ends of the coronary arteries and the branches that extend therefrom. The distal ends of the coronary arteries for a particular patient may have different colors, e.g., anywhere from red to blue, depending on the local values of computed LNS determined for the respective distal ends. Thus, an FFR computed in the aorta may be a high value (e.g., 1), whereas the FFR values may drop as one moves downstream form the aorta, along the coronary arteries. High FFR values, like low LNS values, may indicate healthy vessel regions.

Based on the metrics of interest displayed on the representation of the vasculature, a user may determine that the computed LNS has dropped below a lower limit used for determining the presence of a functionally significant lesion or other feature that may require intervention (e.g., based on the location(s) of areas colored red or otherwise indicating a value that is below the lower limit), and the user may also be able to locate the functionally significant lesion(s). Alternatively or additionally, the user may locate the functionally significant lesion(s) based on the geometry of the artery or branch.

Step 212 may include enabling the assessment of treatment options based on the one or more metrics of interest. For example, step 212 may involve presenting a user interface that would allow the user to select the location for a proposed treatment on the vasculature, select the parameters for treatment, and/or simulate the results of the treatment. The assessment of various treatment options may also include, for example, an optimization of a treatment based on the simulation of results for various treatment options. In one embodiment, step 212 may involve determining a treatment option (e.g., a suggested lesion to treat) based on the identified metrics (e.g., as calculated in steps 204, 206, and 208), and/or outputting the determined treatment option to display or an electronic storage medium. FIGS. 6A-6H and their accompanying descriptions may describe at least some embodiments of functionalities of a user interface for identifying anatomically relevant blood flow characteristics and assessing treatment options.

FIG. 3 is a block diagram of a general method 300 of determining location(s) of diseased region(s) in the vasculature, according to an exemplary embodiment of the present disclosure. In some embodiments, one or more steps of method 300 may also be used to determine the extent or range of the diseased region(s), by calculating a lumen narrowing score. Thus, method 300 may provide at least some embodiments for performing step 206 of method 200, as depicted in FIG. 2.

Step 302 may include identifying a lumen and/or a centerline of a vessel from the received representation of the vasculature. Various segmentation methods (e.g., marching cubes algorithm) may be used to identify the lumen and/or the centerline of a vessel. The segmentation may be based on the intensity variation of medical images received from a medical scanning modality. For example, the process of identifying the lumen and/or centerline via segmentation and/or image processing may use methods disclosed, for example, in U.S. Pat. No. 8,315,812 issued Nov. 20, 2012, entitled "Method and System for Patient-Specific Modeling of Blood Flow," which is incorporated by reference in its entirety. The representation may include a model or an image data received, for example, in step 202 of method 200.

Step 304 may include receiving lumen measurements (e.g., of the lumen's radius, circumference, size, and/or area) along the centerline of the vessel. The measurements may be made manually or automatically using an image processor analyzing the received representation. The measured (or observed) lumen radius, circumference, and/or area may be used in subsequent calculations, e.g., lumen narrowing score, by comparing it to the healthy or ideal lumen radius, circumference, or area. In some embodiments, other metrics (e.g., torsion, elliptical area, etc.) may be used in the comparison between the measured or observed lumen and the healthy or ideal lumen, and the steps of method 300 may be modified accordingly.

Step 306 may include predicting the healthy (or ideal) lumen measurement. In various embodiments of the present disclosure, a lumen measurement may include, for example, the radius, diameter, circumference, area, torsion, one or both of an elliptical radius, etc. In some embodiments, the thickness and/or density of the vessel wall may be factored into the lumen measurement. The prediction of the healthy lumen measurement (e.g., radius, circumference, and/or area) may be based on the observed lumen radius, circumference, and/or area observed from annotated image data and/or from known healthy lumen measurements. While the following embodiments describe steps based on a healthy lumen radius, the methods may be applied to any lumen measurement.

The healthy lumen radius may be calculated using one or more methods. For example, the healthy lumen radius may be calculated using a kernel regression of the lumen areas (e.g., as in 306A) across possible vessel pathways (e.g., from ostium to the leaves). Method 400, as depicted in FIG. 4A may provide a more detailed explanation of at least some embodiments for performing step 306A (e.g., a kernel regression of lumen areas).

Additionally or alternatively, step 306 may involve using a machine learning algorithm trained along healthy vessel sections (e.g., as in step 306B) to calculate the healthy lumen radius, $r_{healthy}(x)$. Other measurements of a healthy lumen or surrounding area may also be used. Method 500, as depicted in FIG. 5 may provide a more detailed explanation of at least some embodiments for performing step 306B (e.g., using machine learning to determine healthy lumen characteristics). As described in method 500, features of the vasculature that are upstream and/or downstream of a given section (e.g., a diseased region) may be mapped to a given section to estimate the healthy vessel radius of what may be a diseased region. These features may be anatomical, physiological, and/or geometrical. In some embodiments, a machine-learning approach may enable a better identification of non-focal stenosis morphologies, e.g., long diffuse lesions, ostial lesions, lesions which are present along an entire section, etc.

Step 308 may include generating lumen narrowing score(s) at one or more points of the vessel based on a comparison of the actual or observed lumen measurement (e.g., radius, diameter, area, etc.) to the predicted healthy lumen measurement (e.g., radius, diameter, area, etc.) along the centerline of the vessels.

For the kernel regression method, a number of lumen narrowing scores (e.g., fifteen) may be calculated by varying the size of Gaussian kernel and accounting for steep drops in bifurcations by convolving the Gaussian kernel with sigmoidal function.

The lumen narrowing score (LNS) may be calculated from the actual and healthy radius as $$\kappa(x) = \frac{r(x)}{r_{healthy}(x)},$$

where $r_{healthy}(x)$ may refer to the theoretical healthy radius of a vessel lumen and r(x) may comprise the radius of the maximum inscribed sphere within the lumen.

In the machine learning method for predicting healthy lumen measurements (e.g., as in step 306B and described in detail further in method 500), the predicted healthy lumen measurements may also be divided by actual or observed lumen measurements to obtain LNS at desired points of a vasculature. Thus, LNS may be a ratio of an actual lumen measurement (e.g., actual radius) to a healthy (or ideal) lumen measurement (e.g., healthy radius).

Step 310 may include determining location(s) of diseased region(s) of the vessel based on the lumen narrowing score(s). For example, a high lumen narrowing score (e.g., one that exceeds a predetermined threshold) may predict the presence or severity of disease at a location or region. In some embodiments, indices or metrics other than the lumen narrowing score may be used for determining location(s) of diseased region(s). For example, an indicia for plaque burden and/or a remodeling index may be used in step 310.

In some embodiments, LNS, or a similar metric, may be used as an input and/or feature for a machine learning algorithm for predicting various other metrics of interest (e.g., FFR, sensitivity, etc.), which may be linked to the centerline points. These other metrics of interest may be used to determine and/or further refine the location, extent or range of diseased region(s). Thus, in such embodiments, both kernel regression and machine learning may be used to determine the location(s) of diseased region(s), resulting in the performance of steps in both method 400 and 500. In further embodiments, LNS, or a similar metric, may be used for identifying trim plane location to ensure that image data is not trimmed or segmented at or near regions of interest (e.g., diseased region(s)), and/or for computing an adapted finite element mesh of the representation of the vasculature or vessel of interest.

Figure 4B:
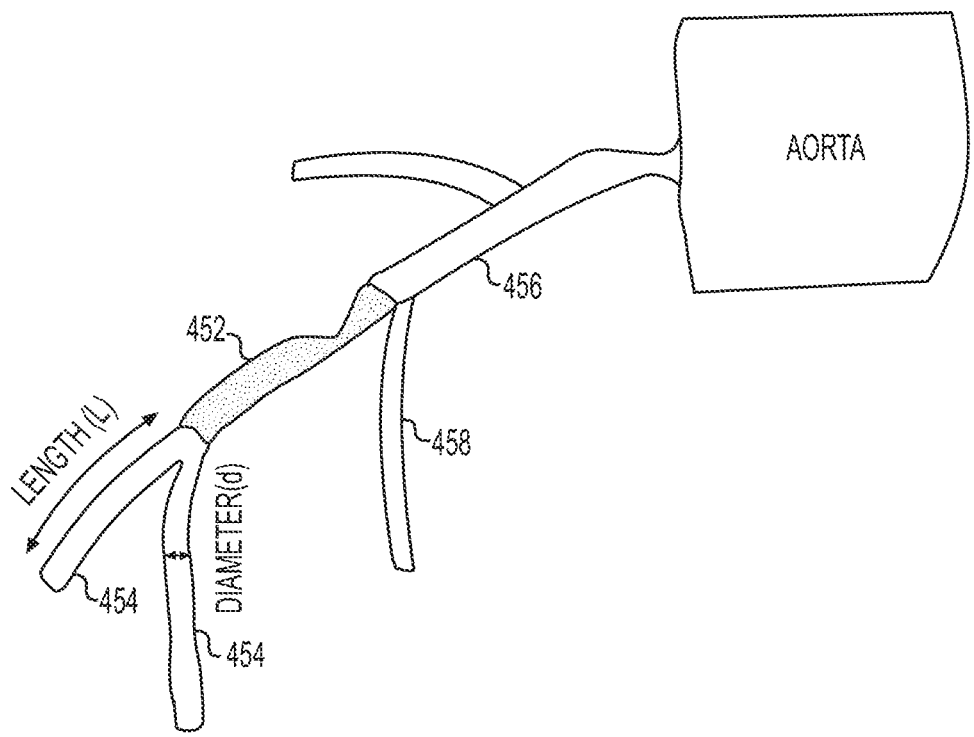
FIG. 4B is an illustration of an exemplary vascular tree network, according to an exemplary embodiment.

FIG. 4A is a block diagram of a general method 400 of predicting a healthy (or ideal) lumen radius using kernel regression. FIG. 4B is an illustration of an exemplary vascular tree network 450 used in various embodiments presented herein, according to an exemplary embodiment. For example, in step 402 of method 400, a vessel lumen may be split into the sections as depicted in FIG. 4B. Thus, for ease of understanding, various embodiments of method 400 may be described with reference to vascular tree network 450.

For purposes of demonstrating at least some embodiments for the calculation of LNS via kernel regression in the following paragraphs, observed or actual lumen radii may be used, e.g., to obtain healthy (or ideal lumen radii at various location(s) of a vasculature. However, it is to be understood that a lumen measurement may also refer to other forms of measurements (e.g., area, size, length, torsion, etc.) of the lumen and/or of areas adjacent to connected to the lumen (e.g., vessel wall). As explained in method 300 depicted in FIG. 3, the LNS may be based on the healthy (or ideal) lumen radius and the observed or actual lumen radius. Thus, method 400 may involve working with the identified lumen of the received representation of the vasculature (e.g., from step 302 of method 300), for which measurements of the lumen's (observed) radius were received (e.g., as in step 304 of method 300).

Referring to FIG. 4A, step 402 may include splitting the vessel into sections or regions based on anatomical characteristics. In one embodiment, to assess the healthy lumen measurement (e.g., radius, diameter, area, etc.,), the vessel may be split into stem-crown-root units, as depicted in FIG. 4B. In some embodiments, the vessel being split may of an entire vasculature.

Referring to FIG. 4B, a stem 452 may refer to a given section or region of a vessel or vasculature being analyzed in method 400A. Thus, a stem 452 may be the section for which a healthy radius or diameter may be predicted. Stem 452 may be defined based on branch points as separators with the corresponding crown 454 and root 456 being the downstream and upstream vasculature, respectively. A sibling vessel 458 may be identified as the other child of the parent vessel. Epicardial volume, length, diameter, and different ratios may be calculated in the crown, root, and/or sibling vessels, and may be assigned as features for a given stem 452.

In performing step 402, the radius of a lumen along the centerline of a vasculature may be modeled, e.g., as a radius curve. Stenosed regions may be characterized by a u-shape in the radius curve. For example, a radius may steadily decrease and then increase, to reflect a vessel narrowing of a stenosed region. However, since diseases could be sharp and abrupt (acute) or long (diffuse), and since radii may have a sharp decrease at bifurcations (dictated by Murray's law), there may be a need for a family of global regressors to infer the lumen narrowing scores.

Thus, step 404 may include forming a plurality of regressors to capture different lengths and locations of lumen narrowing. For example, regressors may include, but are not limited to, a global kernel fit (e.g., 404A), segmental fit (e.g., 404B), and anisotropic kernel fit (e.g., 404C).

A global kernel fit 404A may be used, e.g., for the entirety of the vessel pathway (e.g., from the root (ostium) to the leaves), where the healthy radius may be computed as:

$$r_{healthy}^{global}(x) = \frac{\sum_{x'=1}^{n} N(x' \mid x, \sigma_x) w_{x'} r_{x'}}{\sum_{x'=1}^{n} N(x' \mid x, \sigma_x) w_{x'}},$$

where $N(.,)$ may be the Gaussian function, $\sigma_x$ may represent a width of the Gaussian kernel, $w_x$, may represent weight functions and r may represent the radius.

A segmental fit 404B may be used for segments between branches. For the segmental fit 404B, the healthy radius may be computed as:

$$r_{healthy}^{segmental}(x) = \frac{\sum_{x'=1}^{n} N(x' \mid x, \sigma_x) I(x', x) w_{x'} r_{x'}}{\sum_{x'=1}^{n} N(x' \mid x, \sigma_x) I(x', x) w_{x'}},$$

where l may refer to the Heaviside function, e.g., $l(x,y)=1$ if $x>y$ and 0 otherwise.

An anisotropic kernel fit 404C for each path from the root to the leaves, but weighted with a sigmoidal function centered at the nearest ostium designed to minimize the effect of sharp radius variation at the branch $$r_{healthy}^{aniso}(x) = \frac{\sum_{x'=1}^{n} N(x' \mid x, \sigma_x) S(x', x) w_{x'} r_{x'}}{\sum_{x'=1}^{n} N(x' \mid x, \sigma_x) S(x', x) w_{x'}},$$

where the sigmoidal function, S, is given by $$S(x', x) = \frac{1}{1 + \alpha e^{-k d_o(x', x)}},$$

and $d_o(x',x)=d(x', x_0)-d(x,x_o)-d(x, x_{up})$, d represents the distance function.

Step 406 may include determining parameter values for each regressor. Five parameters for $\sigma_x$, $\sigma_{max}$ and $r_{x,max}$ may be chosen for each of the regressors, and hence make a total of 15 regressors. The parameter values chosen for each of the regressors may include, for example, $\sigma_x=5.0*(1+(n-3)*0.4)$, $\sigma_{max}=200.0*(1+(n-3)*0.4)$, $\sigma_r=0.25*(1+(n-3)*0.4)$, and $k=0.1+n*0.3$, where $n$ ranges from 1 to 15.

Thus, the different regressors and/or their corresponding parameter values may ensure the capturing of different lengths and locations of lumen narrowing.

Step 408 may include predicting a healthy (or ideal) lumen measurement using the different regressors and/or their corresponding parameter values. The global healthy radius may be used to predict a healthy lumen measurement, e.g., at a point, x, along the centerline of a vessel. Alternatively or additional, a segmental healthy radius (using segmental fit 404B) or anisotropic healthy radius (using anisotropic fit 404C) may also be used to predict a healthy lumen measurement at a point, x, along the centerline of a vessel.

Step 410 may include determining a lumen narrowing score (LNS) using the predicted healthy lumen measurement. In some embodiments, once the global healthy radius, $r^*_{healthy}(x)$ is calculated, a corresponding health index score, $$\kappa(x) = \frac{r(x)}{r^*_{healthy}(x)}$$

may be calculated. From the health index score, the lumen narrowing score ($\lambda$) may be determined as $\lambda(x)=1-\kappa(x)$ if $\kappa(x)<=1$, otherwise, $\lambda(x)=0$. Thus, if the actual lumen measurements were to equal the healthy or ideal lumen measurement, the health index score may be one. A health index score of 1 may yield a lumen narrowing score of zero, which may signify the absence of disease (as may be expected if the actual lumen measurements reflect the healthy/ideal lumen measurement).

FIG. 5 is a block diagram of a general methods for training a machine learning algorithm to predict a healthy (or ideal) lumen measurement. Moreover, the training and application of the machine learning algorithm to predict a healthy (or ideal) lumen measurement may be split into training phase 500 (of training the machine learning algorithm) and application phase 550 (of using the trained machine learning algorithm for a patient). The training phase involves, for example, the training of a machine learning algorithm using a training data set comprising of domain and range data. The domain data may include, for example, a list of features that may be predictive of healthy lumen measurements, and the range data may include the healthy lumen measurements. The training data may be population-derived (e.g., from a plurality of individuals), or may come from the patient seeing analysis (e.g., the patient from whom healthy lumen measurements are being sought. Like step 402 in method 400, method 500 may involve receiving representation(s) (e.g., image data and/or vascular models) of a vasculature and initially splitting the lumen into sections or regions based on anatomical characteristics. In one embodiment, the lumen may be split into stem-crown-root units, as depicted in FIG. 4B and explained above. The representation(s) may be of each a plurality of individuals (e.g., for training phase 500) or of a patient for whom the healthy lumen measurements are desired to be predicted (e.g., for application phase 550).

Referring to training phase 500 of FIG. 5, step 502 may include acquiring representation(s) of vasculature(s) having at least a healthy region, one or more features upstream and/or downstream of the healthy region for each representation, and lumen measurements of the healthy region, for each of the representation. Each representation may be of an individual of a plurality of individuals (e.g., for a population derived training data), and may be image data or a vascular model. The vasculature and/or healthy region for each of the representations may correspond with one another. For example, for each of a plurality of individuals, a representation of a coronary vasculature may be acquired having a healthy region on a given vessel. Furthermore, the vasculature and/or healthy region acquired for each of a plurality of individuals in the training phase 500 may correspond with the vasculature and/or healthy region acquired (or to be acquired) in the application phase 550, as will be explained later.

It is contemplated that the features acquired in step 502 may be defined for each vessel section or for one or more location(s) of a vessel section. These features may be anatomical, physiological, and/or geometrical. Examples of geometric features may include, but are not limited to, distance from the nearest bifurcation, distance from the ostium, minimum upstream diameter, etc. The features may include a numerical description of the patient-specific geometry at a vessel section or one or more point(s) of a vessel section. In some embodiments, manually annotated healthy and/or diseased sections from population-derived vasculature representations may be used as ground truth for geometric features. In such embodiments, trained readers may assess the vasculature of patients and may deem each section of vessel lumen as either being diseased or healthy. Physiological features may include boundary conditions (inflow boundary conditions, outflow boundary conditions, vessel wall boundary conditions, etc.), blood flow characteristics (e.g., flow rate, pressure, etc.), hemodynamic characteristics (e.g., wall shear stress, strain, etc.). Anatomical features may include, but are not limited to, characteristics of the vessel, image intensity, vessel measurements, etc. Furthermore, the features may be determined upstream and/or downstream of a given section (e.g., a healthy region of the plurality of individuals corresponding to a diseased region in a patient's vasculature). That is, the features may include geometrical, physiological, and/or anatomical measurements at location(s) upstream and/or downstream of a given section that are predictive of the lumen measurements at the given section.

Additionally or alternatively, these features may include received values of one or more metrics of interest associated with one or more locations in the patient's vasculature or vessel of interest (e.g., from step 204 of method 200, as depicted in FIG. 2). Thus, these metrics may include, for example, FFR, iFR, CFR, an anatomical characteristic, a plaque characteristic, a metric for radiodensity, and/or a blood flow characteristic.

Additionally or alternative, the features may include (i) biographical characteristics: patient age, gender, height, weight, etc.; (ii) disease characteristics: presence or absence of diabetes, myocardial infarction, malignant and rheumatic conditions, peripheral vascular conditions, etc.; (iii) lifestyle characteristics: presence or absence of current medications/drugs, smoker/non-smoker; (iv) hemodynamic forces: axial plaque stress, wall shear stress, etc., (v) systolic and diastolic blood pressures; and/or (vi) blood properties including: plasma, red blood cells (erythrocytes), hematocrit, white blood cells (leukocytes) and platelets (thrombocytes), viscosity, yield stress.

The defining features may be associated with location(s) on a vessel section having a healthy (or ideal) lumen measurement. Since the vasculature used may be based on population-derived data with known healthy lumen measurements, it is contemplated that the healthy regions of the vasculature may be known and/or may be identified. However, in some embodiments, features may be defined for a given section (segment), where each section may represent coronary segmentation between bifurcations. Since the flow rate in a given section may be constant, a healthy vessel may maintain its radius within a section, e.g., to preserve a homeostatic state of wall shear stress. Thus, bifurcations may be used as separators for sections and/or regions.

Additionally, step 502 may include receiving lumen measurements of the healthy region. The lumen measurements may be directly measured or estimated from the vascular representations of each of the plurality of individuals, or derived, otherwise from population-data, reference materials, or from healthy regions of the patient's vasculature. In some embodiments, a lumen's measurement (e.g., radius, diameter, area, etc.) may be calculated, e.g., using maximum inscribed spheres. Alternatively or additionally, the average lumen measurement may be derived from the area of lumen along the normal to centerlines, in order to determine features for the machine learning algorithm. It is contemplated that in some embodiments, population-derived data may be used to determine accurate values for lumen measurements near bifurcations, to enable the identification of non-focal stenosis morphologies.

In some embodiments, step 504 may include forming a feature vector of the defined features at one or more location(s) along a vessel. These location(s) may be, for example, upstream and/or downstream of a given section. In some embodiments, the given section would be a healthy region of the vasculature for each of the vasculatures used in the training phase 500, but may correspond with a diseased region of the vasculature of a patient in the application phase 550. The feature vector may contain both global and local features, where: for global features, location(s) along the vessel may have the same numerical value (e.g., for a section or region of the vessel); and for local features, the value(s) may change at different location(s) in the feature vector. For example, a global feature may include biographical or lifestyle characteristics, whereas a local feature may include geometric, physiological, and/or anatomical characteristics.

Step 506 may include associating the features and/or feature vectors with lumen measurements at location(s) in the healthy region. Thus, the defined features of the vasculature may be mapped (or associated) to their corresponding healthy lumen measurements (e.g., radius, area, etc.) at the point(s) and/or section(s) having the defined features. The corresponding healthy lumen measurements, received in step 502, may be directly measured or estimated from the vascular representations of each of the plurality of individuals, or derived, otherwise from population-data, reference materials, or from healthy regions of the patient's vasculature.

Thus, steps 502 through 506 may provide a training data set comprising of features (e.g., domain), and healthy lumen measurements (e.g., range) for the training of a machine learning algorithm (e.g., as explained in step 508, herein). The training data set may be measured, obtained, and/or calculated from the vasculature of each of the plurality of individuals, for example, at the an identified healthy region, and/or location(s) upstream and/or downstream of the identified healthy region. It is contemplated that the patient for whom analysis is being sought in application phase 550 may be one of the plurality of individuals. Alternatively, instead of obtaining the training data set from a plurality of individuals, some embodiments envision obtaining this training data and associating feature vectors, from healthy regions of the vasculature of a patient. Thus, in such embodiments, training data from a healthy region of the patient's vasculature may be used to train a machine learning algorithm to predict healthy (or ideal) lumen measurements in a diseased region of the patient's vasculature.

Thus sections in a patient-specific vasculature (e.g., of the patient or each of the plurality of individuals) may be represented in a parameter space, and its features may be associated or mapped to healthy lumen measurements. In the training phase 500, the association or mapping may enable learning of the relations and/or predictability between the features and their associated healthy lumen measurement. In the application phase 550, the trained machine learning algorithm may be used in the diseased region of the vascular representation of the patient to provide more accurate or refined definition of regions of disease in long diffuse lesions, ostial lesions, or lesions which are present along an entire section.

Step 508 may include training a machine-learning algorithm to predict healthy or ideal lumen measurements at a section or region of a vessel (e.g., diseased region), or at one or more points of a vessel from features of the vessel. The training may use the associated features from step 506, for example, to determine relations and/or feature weights. Examples of machine learning algorithms that can perform this task are support vector machines (SVMs), neural networks, multi-layer perceptrons (MLPs), multivariate regression (MVR) (e.g., weighted linear or logistic regression), and/or other supervised machine learning techniques known to persons having ordinary skill in the art. In one embodiment, random decision forests may be used for the training of the machine learning algorithm. For example, one method may be used for the non-terminal vessels and another method may be used for ostial segments. Server systems 106 may then save the results of the machine-learning algorithm (e.g., feature weights) to a digital representation (e.g., the memory or digital storage (e.g., hard drive, network drive) of a computational device such as a computer, laptop, DSP, server, etc.). The stored feature weights may define the extent to which features (e.g., geometrical characteristics, anatomical characteristics, physiological characteristics, biographical characteristics, hemodynamic characteristics, etc.) are predictive of the lumen measurements at one or more points of the vasculature, vessel, or section of the vessel.

Step 510 may include outputting the trained machine learning algorithm (e.g., to an electronic storage medium). The trained machine learning algorithm may be used in the application phase 550, e.g., in step 556, to predict the healthy lumen measurements for diseased region(s) of the lumen, vasculature, or vessel of the patient.

For example, step 552 may include acquiring or receiving a patient-specific representation of a vasculature having a diseased region, and a list of features associated with locations of the patient's vasculature. It is contemplated that the location(s) of diseased region(s) in the patient's vasculature may not be known or may only be partially known or estimated prior to applying the machine learning algorithm. In some embodiments, where diseased region(s) of a patient's vasculature may be partially known or estimated, and where machine learning based methods are performed to gain a more precise location of the diseased regions, the features may be upstream and/or downstream of the partially known or estimated diseased region. The vasculature may of a patient for which locating a diseased region (e.g., using LNS) is desired. The types of features in step 552 may correspond to the type of features defined in step 502 in the training phase 500 for the machine learning algorithm.

At step 554, the features (and their values or characteristics) may be compiled into feature vector(s) at one or more points of the patient's vasculature. Thus, step 554 may include creating a feature vector of the features used in the training model at one or more location(s) of the patient's vasculature. In some embodiments, a feature vector would include features (and their values) at location(s) upstream and/or downstream of a segment of the patient's vasculature that would be predictive of the healthy lumen measurement at the location on the segment.

Step 556 may include using the saved results of the trained machine learning algorithm (e.g., from step 508) to predict healthy lumen measurements in the patient's vasculature. In some embodiments, the healthy lumen measurements may be at location(s) of the diseased region(s) at which the feature vectors were formed, the feature vectors comprising of features upstream and/or downstream of the diseased region. Thus, step 556 may include inputting the received features (or formed feature vectors) into the trained machine learning algorithm (e.g., trained and outputted in steps 508 and 510, respectively) to predict the healthy (or ideal) lumen measurements for a location in the patient's vasculature.

The predicted healthy (or ideal) lumen measurements may then be used to locate, refine, and/or track the locations and/or extent of diseased region(s) according to methods presented above. It is contemplated that the machine learning algorithm may be applied iteratively to obtain more precise location(s) or extent of the diseased region(s). The predicted healthy (or ideal) lumen measurements may be displayed or stored in an electronic storage medium.

In some embodiments, step 558 may include computing and outputting a lumen narrowing score (LNS), using the predicted healthy lumen measurements. As explained above, an LNS may be based on a ratio of an observed (or actual) lumen measurement, and the healthy (or ideal) lumen measurement. It is contemplated that the observed (or actual) lumen measurement may be readily measured from the representation of the vasculature of the patient, or may be computed or modeled using methods disclosed, for example, in U.S. Pat. No. 8,315,812 issued Nov. 20, 2012, entitled "Method and System for Patient-Specific Modeling of Blood Flow," which is incorporated by reference in its entirety. An LNS may indicate whether there a point or area of a vessel or lumen is a part of a diseased region. Various metrics of interest may indicate the extent or range of the diseased region.

It is contemplated that in some embodiments, a trained machine learning algorithm that predicts healthy lumen measurements from features of a vessel may merely be received, e.g., in an electronic storage medium, and readily implemented in step 556 in application phase 550. In such embodiments, the training of such a machine-learning algorithm by server systems 106 may be rendered unnecessary.

FIGS. 6A-6H are illustrations of exemplary user interfaces for identifying an analyzing anatomically relevant blood flow characteristics in a patient, and/or to plan treatment options.

For example, in FIG. 6A, a three dimensional marker (e.g., Stenosis Marker 602) may indicate the location of a maximal anatomical stenosis within a range (e.g., above 30%), when comparing the diameter of the vessel from CCTA versus the diameter of the healthy (or idealized) vessel. The range may be predetermined and/or selected by a user. Measurements for the healthy (or idealized) vessel may be computed using methods described above (e.g., method 300 as depicted in FIG. 3). The computerized tomography based fractional flow reserve (FFR-CT) pin 604 distal to Stenosis Marker 602 may indicate the point of FFR-CT recovery. It is contemplated that in region(s) distal to the throat (e.g., minimum lumen diameter) of the stenosis, the pressure may increase. The recovery region may typically be a small region distal to the minimum luminal diameter. Thus, in some embodiments, the pressure just distal to the recovery region may be measured in order to avoid the fluctuation of pressure within this region.

Clicking on Stenosis Marker 602 or distal FFR-CT pin 604 in the exemplary user interface depicted in FIG. 6A may reveal additional information about that stenosis (e.g., as depicted in FIG. 6B). For example, FIG. 6B reveals the FFR-CT value proximal to the stenosis (e.g., as in marker 606), the FFR-CT gradient (ΔFFR-CT) across the stenosis (e.g., as in marker 608), an indicator of the percentage of myocardium that may be at risk, for example, due to a diseased region (e.g., "% Myocardium at Risk") at that stenosis (e.g., as provided by plan marker 610), and the percent stenosis ("% Stenosis" 612). Thus, a user can interact with various manipulator handles on the user interface (e.g., as in marker 606) to change the range that may be used to determine the values. As the user changes the range, various functionalities may be updated. For example, the UI may be updated to reflect the new range 614. For example, the location of Stenosis Marker 602 may automatically translate or relocate to the location of a maximal anatomical stenosis within the user-defined range. The manipulator handles may be round UI assets that may define the pin's point of inspection on the model surface. For example, markers 604 and 606 can both have handles, and there may also be a handle in between these markers. Furthermore, a user may be able to modify the an anatomy of the vasculature, e.g., % stenosis 612, using various tools for virtual modification of the lumen.

Figure 6D:

Referring now to FIG. 6D, a user interface may also communicate anatomical sizing information (e.g., as in marker 616), for example, a diameter, a length, a cross-sectional area, a minimum diameter, a reference diameter (of the idealized or healthy model, vasculature, vessel, or lumen) and an average reference diameter.

Figure 6E:

FIGS. 6D and 6E are illustrations of exemplary user interfaces depicting configuration options for plan (e.g., as in FIG. 6D) and size (e.g., as in FIG. 6E). In these exemplary user interfaces, "plan" configuration options may refer to functionalities for displaying physiological features, blood flow characteristics (e.g., FFR-CT gradient (ΔFFRct) 624), image characteristics (e.g., image quality 622) and/or disease characteristics (e.g., max stenosis 618, percentage of the myocardium at risk (e.g., "myocardium 620"), etc.), and "size" configuration options may refer to functionalities for displaying anatomical or geometrical characteristics (e.g., vessel or luminal measurements). For example, in the exemplary user interface depicted in FIG. 6D, a user may choose the configuration or display option for, and/or toggle on or off, a maximum stenosis 618, a percentage of the myocardium that is at risk (e.g., "myocardium" 620), an image quality (e.g., resolution, magnification, etc.) 622, or an FFR-CT gradient (ΔFFRct) 624. In the exemplary user interface depicted in FIG. 6E, a user may toggle on or off, the display of, a minimum diameter 626, a reference (e.g., ideal or healthy) diameter 628, an average reference diameter 630, a minimum luminal diameter (MLD) 632 or a cross-sectional area 634. It is contemplated that the list of options or configurations is not limited to those discussed above, and nor is it incumbent for user interfaces described in various embodiments presented herein to necessarily include all the options displayed, e.g., in FIGS. 6D and 6E.

Figure 6F:
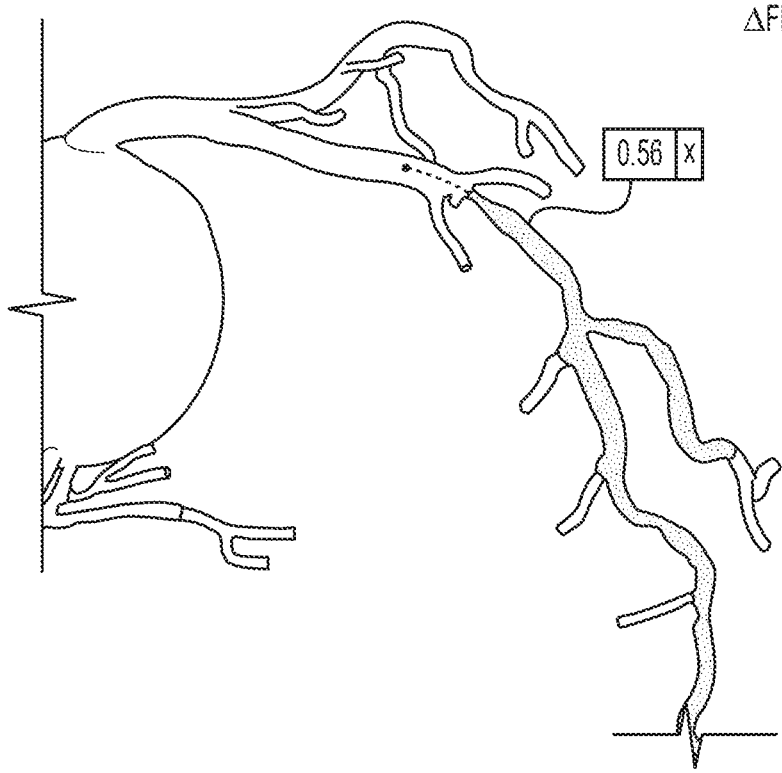

For example, FIG. 6F depicts an exemplary user interface with an expansion of the functionalities for display. These functionalities may include anatomical characteristics and disease characteristics. Thus, FIG. 6F depicts an exemplary user interface displaying a coronary vascular tree with the metrics for a diameter proximal to a diseased region (e.g., "Prox Diam" 636), a diameter distal to a diseased region (e.g., "Dist Diam" 638), an average reference diameter ("Ave Ref Diam" 640), minimum diameter 642, length 644 (e.g., of a selected vessel section), a lumen narrowing score (LNS) (e.g., a max LNS 646), an average reference stenosis 648, maximum reference stenosis 650, and an FFR-CT gradient (ΔFFRct) 652. It is also contemplated that user interfaces displaying a vasculature and/or vessels of interest may enable a user to rotate, magnify, or change the perspective, projection, and/or angulation of the display (e.g., as in FIG. 6G).

Figure 6G:
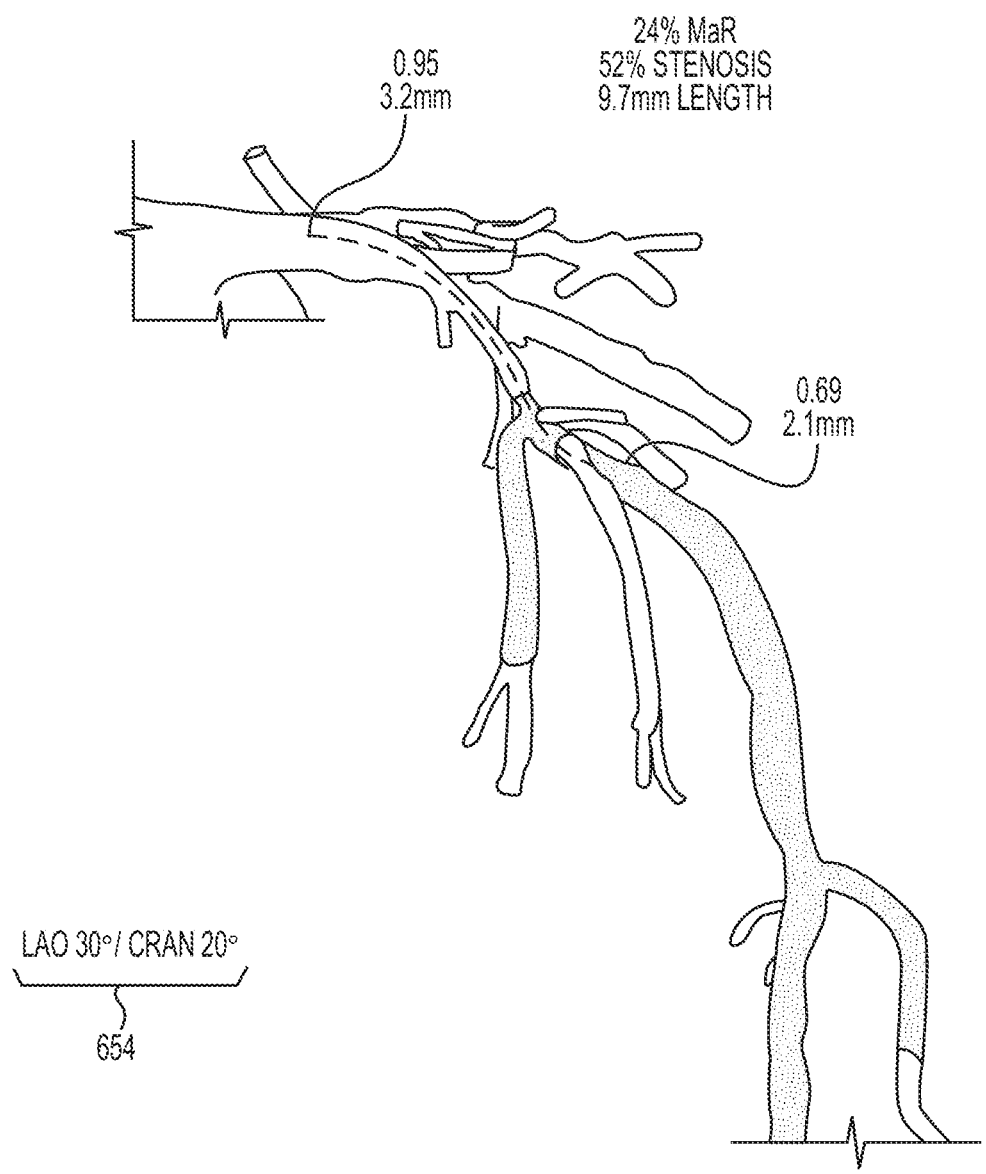

FIG. 6G depicts an exemplary user interface displaying a coronary vascular tree with metrics of interest. These metrics may include the metrics discussed in FIGS. 6D-6F. However, the user interface depicted in FIG. 6G may expand upon the discussed functionalities by providing a view 654 view of a given vasculature using left anterior oblique (LAO) projection and cranial (CRAN) angulation. The user interface may also enable a user to view the representation of the vasculature in other perspective, projections, and/or angulations.

Figure 6H:
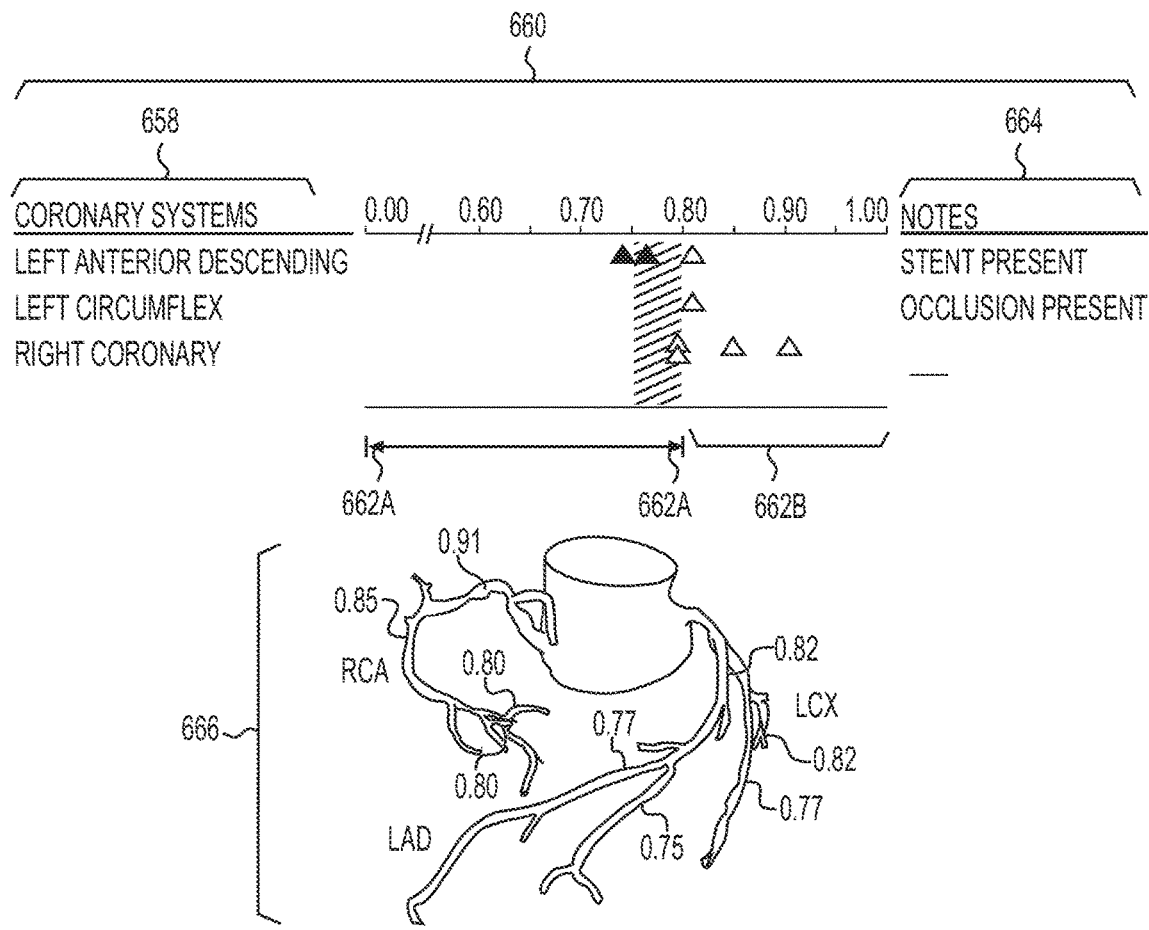

FIG. 6H depicts an exemplary user interface providing information pertaining to a vasculature of a patient ("John Doe"), as an overview. The summary may provide biographical details 656 about the patient, e.g., to facilitate patient identification. As exemplified in FIG. 6H, a user interface may present anatomically relevant blood flow characteristics in multiple forms, for example, as a table depicted in 660. In one embodiment, as depicted in FIG. 6H, table 660 may summarize the functional significance of various coronary systems. For example, a coronary vascular network 658 may be categorized into the left anterior descending system, left circumflex system, and right coronary system. The table 660 may identify specific regions, vessels, or systems of any vascular network. Furthermore, table 660 may depict the values of a metric of interest for various pins placed at locations in the vasculature for a given coronary system (or similar regions, vessels, or systems of a given vasculature). Table 660 may indicate values or measurements of the metric of interest which are functionally significant 662A or are not functionally significant 662B. Alternatively or additionally, table 660 may also indicate what values or measurements of the metric of interest exceed or do not exceed a predetermined threshold. Furthermore, table 660 may also be accompanied by notes 664 that may aid a physician or medical personnel in the interpretation of the table or chart, or may serve as a means for one to record. A user interface depicting a summary report may also depict a representation (e.g., a model) of the vasculature or vascular network 666, with pins measuring a metric of interest. The vasculature or vascular network may also be labeled, e.g., to indicate various regions or systems of vessels (e.g., left anterior descending (LAD), right coronary artery (RCA), left circumflex (LCX), etc.). In some embodiments, the vasculature or vascular network may be color coded to show differences in a metric of interest (e.g., FFR-CT).

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method of identifying anatomically relevant blood flow characteristics in a patient, the method comprising:

receiving, in an electronic storage medium, a first patient-specific representation of at least a portion of vasculature of the patient having a lesion at one or more points, the first patient-specific representation including a plurality of features of the at least a portion of the vasculature, the plurality of features including one or more of an anatomical, physiological, or geometrical feature, wherein the plurality of features includes a bifurcation;

determining a location of a diseased region in the vasculature of the patient, by:

receiving one or more observed lumen measurements of the vasculature of the patient, each observed lumen measurement corresponding to a respective position along a blood vessel of the at least portion of vasculature of the patient based on the first patient-specific representation;

predicting a second patient-specific representation of at least a portion of the vasculature of the patient in a healthy condition by inputting the plurality of features of the first patient-specific representation into a trained machine learning algorithm, wherein:

the second patient-specific representation includes one or more healthy lumen measurements of the vasculature of the patient; and each healthy lumen measurement in the second patient-specific representation corresponds to a respective one of the observed lumen measurements in the first patient-specific representation;

generating a respective lumen narrowing score for each position along the blood vessel based on a comparison of each observed lumen measurement and the corresponding healthy lumen measurement;

determining a location of the lesion along the blood vessel based on the generated one or more lumen narrowing scores;

determining, based on the generated one or more lumen narrowing scores, a distal bound of the lesion;

automatically determining that the bifurcation is within a first predetermined distance beyond the determined distal bound in a distal direction;

automatically determining a first distal position on the first vessel that is the first predetermined distance beyond the determined distal bound;

automatically determining a second distal position on the second vessel that is the first predetermined distance beyond the determined distal bound; and generating a visualization of at least the diseased region, the visualization including:

the first vessel and the second vessel;

a first distal pin displayed on the first vessel at the determined first distal position; and a second distal pin displayed on the second vessel at the determined second distal position.

2. The computer-implemented method of claim 1, further comprising:

determining, based on the generated one or more lumen narrowing scores, a proximal bound of the lesion, automatically determining a proximal position that is the first predetermined distance beyond the determined proximal bound in a proximal direction;

wherein determining the distal bound and the proximal bound includes determining where an acuity of the lesion no longer exceeds a predetermined threshold, wherein the acuity of the diseased region is characterized by the generated one or more lumen narrowing scores;

and determining an extent of the diseased region using the proximal position, the first distal position, and the second distal position.

3. The computer-implemented method of claim 1, wherein:

predicting the second patient-specific representation further includes inputting a metric of interest associated with one or more locations in the vasculature of the patient into the trained machine learning algorithm, and the visualization of the diseased region includes a display of the metric of interest associated with the first distal position of the first distal pin.

4. The computer-implemented method of claim 3, further comprising:
provide interactive options to change one or more of range, magnification, or angle of the visualization of the diseased region, wherein the first distal pin in the visualization is moveable by a user.

5. The computer-implemented method of claim 1, wherein:
predicting the second patient-specific representation further includes inputting a metric of interest associated with one or more locations in the vasculature of the patient into the trained machine learning algorithm,
the method includes enabling an assessment of treatment options for the diseased region based on the metric of interest, and
the metric includes one or more of:
a function of fractional flow reserve (FFR), including FFR, distal point of FFR recovery, or a delta or change in FFR;
an instant wave free ratio (iFR);
a coronary flow reserve (CFR);
an anatomical characteristic including one or more of a vessel size or vessel thickness;
a plaque characteristic including one or more of a local calcium score, local low intensity plaque score, a measure of spotty calcification, a remodeling index, and/or an indicia of plaque signs;
a radiodensity; and/or
a blood flow characteristic including one or more of a blood flow rate or velocity, or a blood pressure.

6. The computer-implemented method of claim 1, wherein each observed lumen measurement and each healthy lumen measurement of the vasculature of the patient respectively includes one or more of a radius, a diameter, an area, a circumference, a length, one or both elliptical radii, a torsion of the lumen, or a minima or maxima of the above.

7. A system for identifying anatomically relevant blood flow characteristics in a patient, the system comprising:
at least one data storage device storing instructions for identifying anatomically relevant blood flow characteristics in a patient; and
at least one processor configured to execute the instructions to perform a method comprising:
receiving, in an electronic storage medium, a first patient-specific representation of at least a portion of vasculature of the patient having a lesion at one or more points, the first patient-specific representation including a plurality of features of the at least a portion of the vasculature, the plurality of features including one or more of an anatomical, physiological, or geometrical feature, wherein the plurality of features includes a bifurcation;
determining a location of a diseased region in the vasculature of the patient, by:
receiving one or more observed lumen measurements of the vasculature of the patient, each observed lumen measurement corresponding to a respective position along a blood vessel of the at least portion of vasculature of the patient based on the first patient-specific representation;
predicting a second patient-specific representation of at least a portion of the vasculature of the patient in a healthy condition by inputting the plurality of features of the first patient-specific representation into a trained machine learning algorithm, wherein:
the second patient-specific representation includes one or more healthy lumen measurements of the vasculature of the patient; and
each healthy lumen measurement in the second patient-specific representation corresponds to a respective one of the observed lumen measurements in the first patient-specific representation;
generating a respective lumen narrowing score for each position along the blood vessel based on a comparison of each observed lumen measurement and the corresponding healthy lumen measurement;
determining a location of the lesion along the blood vessel based on the generated one or more lumen narrowing scores;
determining, based on the generated one or more lumen narrowing scores, a distal bound of the lesion;
automatically determining that the bifurcation is within a first predetermined distance beyond the determined distal bound in a distal direction;
automatically determining a first distal position on the first vessel that is the first predetermined distance beyond the determined distal bound;
automatically determining a second distal position on the second vessel that is the first predetermined distance beyond the determined distal bound; and
generating a visualization of at least the diseased region, the visualization including:
the first vessel and the second vessel;
a first distal pin displayed on the first vessel at the determined first distal position; and
a second distal pin displayed on the second vessel at the determined second distal position.

8. The method of claim 1, wherein:
the trained machine learning algorithm has been trained, based on (a) features of patient-specific representations of each of a plurality of individuals, (b) healthy lumen measurements of a healthy vessel region of each of the plurality of individuals, and (c) features upstream and/or downstream of the healthy vessel region for each of the plurality of individuals, to learn relations between the features and associated healthy lumen measurements;
the trained machine learning algorithm has been configured to predict the second patient-specific representation using the learned relations; and
a position of each healthy lumen measurement is at a same position in the vasculature of the patient as a position in the vasculature of the patient of the corresponding observed lumen measurement.

9. The method of claim 8, wherein:
the features of patient-specific representations of each of the plurality of individuals for the trained machine learning algorithm are acquired from image data or a vasculature model of each of the plurality of individuals,
the image data has been manually annotated from trained readers, and
the acquired features include at least one of distance from a nearest bifurcation, distance from an ostium, minimum upstream diameter, inflow boundary conditions, outflow boundary conditions, vessel wall boundary conditions, average downstream area, crown volume, or a relationship between parent to daughter vessels in healthy vasculature.

10. The method of claim 8, wherein the features of patient-specific representations of each of the plurality of individuals for the trained machine learning algorithm include at least one of anatomical features, geometrical features, boundary conditions, blood flow characteristics, hemodynamic characteristics, biographical characteristics, diseases characteristics, lifestyle characteristics, hemodynamic forces, or systolic and diastolic blood pressures.

11. The method of claim 8, wherein, for a given location in the healthy vessel region of each of the plurality of individuals, the features that the trained machine learning algorithm is based on are used to create a feature vector, which is associated with a healthy lumen measurement at the given location, and wherein the trained machine learning algorithm has been configured to predict the second patient-specific representation based on the created feature vectors.

12. The method of claim 1, further comprising:
determining, based on the generated one or more lumen narrowing scores, a proximal bound of the lesion; and
automatically determining a first proximal position that is the first predetermined distance beyond the determined proximal bound in a proximal direction, wherein the visualization includes a first proximal pin displayed at the determined first proximal position.

13. The method of claim 1, further comprising:
determining, based on the generated one or more lumen narrowing scores, a proximal bound of the lesion;
automatically determining that the proximal bound is within a second predetermined distance of a secondary distal bound of a secondary lesion;
determining a secondary proximal bound of the secondary lesion; and
automatically determining a proximal position that is the first predetermined distance beyond the determined secondary proximal bound, wherein the visualization includes a proximal pin displayed at the determined secondary proximal bound.

14. The method of claim 1, further comprising:
receiving a function of fractional flow reserve (FFR) value at a plurality of locations along the blood vessel, the plurality of positions including the first distal position; and
displaying the FFR value associated with the first distal position.

15. The method of claim 1, further comprising:
determining, based on the generated one or more lumen narrowing scores, a proximal bound of the lesion;
determining a secondary distal bound of a secondary lesion;
automatically determining that the proximal bound is within a second predetermined distance of the secondary distal bound of the secondary lesion;
determining that the lesion and the secondary lesion are located on a main vessel path; and
determining an FFR pin position at a location having a largest diameter between the determined proximal bound of the lesion and the determined distal bound of the secondary lesion, wherein the visualization includes an FFR pin displayed on the main vessel path at the determined FFR pin position, and the visualization includes a fractional flow reserve (FFR) value at the FFR pin position.

16. The method of claim 1, further comprising determining a severity of the lesion, wherein the first predetermined distance is based on the determined severity.

17. The method of claim 1, wherein generating the lumen narrowing score includes convolving a Gaussian kernel and a sigmoidal function to account for the bifurcation.

18. The method of claim 1, wherein:
the first distal pin is displayed at a centerline of the first vessel and includes a lead line extending from the centerline,
the second distal pin is displayed at a centerline of the second vessel and includes a lead line extending from the centerline,
the first distal pin is moveable by a user, and
the second distal pin is moveable by the user independently from a movement of the first distal pin.

19. A computer-implemented method of identifying anatomically relevant blood flow characteristics in a patient, the method comprising:
receiving, in an electronic storage medium, a first patient-specific representation of at least a portion of vasculature of the patient having a first lesion at a first location and a second lesion at a second location, the first patient-specific representation including a plurality of features of the at least a portion of the vasculature, the plurality of features including one or more of an anatomical, physiological, or geometrical feature;
determining a location of a diseased region in the vasculature of the patient, by:
receiving one or more observed lumen measurements of the vasculature of the patient, each observed lumen measurement corresponding to a respective position along a blood vessel of the at least portion of vasculature of the patient based on the first patient-specific representation;
predicting a second patient-specific representation of at least a portion of the vasculature of the patient in a healthy condition by inputting the plurality of features of the first patient-specific representation into a trained machine learning algorithm, wherein:
the second patient-specific representation includes one or more healthy lumen measurements of the vasculature of the patient; and
each healthy lumen measurement in the second patient-specific representation corresponds to a respective one of the observed lumen measurements in the first patient-specific representation;
generating a respective lumen narrowing score for each position along the blood vessel based on a comparison of each observed lumen measurement and the corresponding healthy lumen measurement;
determining, based on the generated one or more lumen narrowing scores, a first distal bound of the first lesion;
determining, based on the generated one or more lumen narrowing scores, a first proximal bound of the first lesion;
determining, based on the generated one or more lumen narrowing scores, a second distal bound of the second lesion;
automatically determining that the first proximal bound is within a first predetermined distance of the second distal bound;
automatically determining that the diseased region includes the first and second lesions;
automatically determining a pin position in the diseased region based on the first proximal bound and the second distal bound; and
generating a visualization of at least the disease region, wherein the visualization includes the first lesion, the second lesion, and at least one pin provided at the determined pin position.

20. The method of claim 19, wherein automatically determining the pin position includes determining, based on the generated lumen narrowing scores, a position having a largest diameter between the determined first proximal bound and the determined second distal bound.

* * * * *